United States Patent [19]

Jones, III et al.

[11] Patent Number: 4,721,668
[45] Date of Patent: Jan. 26, 1988

[54] PRE-ELECTROPHORETIC NUCLEIC ACID HYBRIDIZATION

[75] Inventors: Frederick S. Jones, III, New York, N.Y.; Jacob I. Grimberg, Passaic, N.J.; John P. Ford, Tappan, N.Y.

[73] Assignee: Lifecodes Corporation, Elmsford, N.Y.

[21] Appl. No.: 634,301

[22] Filed: Jul. 25, 1984

[51] Int. Cl.$^4$ ................................................ C12Q 1/68
[52] U.S. Cl. ........................................ 435/6; 204/1 T; 436/501
[58] Field of Search .............. 435/6; 436/501; 935/78; 204/1 T

[56] References Cited

U.S. PATENT DOCUMENTS 4,563,417  1/1986  Albarella et al. .................. 935/78 X

OTHER PUBLICATIONS

Lewin (1983), In: *Genes* pp. 40–42, 51–52.
Noyes et al. (1975), Cell 5: 301–310.
Harris et al. (1978) Biochemistry 17(16): 3250–3256.
Vieira et al. (1982) Gene 19: 259–268.
Southern (1975), J. Mol. Biol 98: 503–517.
Alwine et al. (1977), Proc. Nat'l. Acad. Sci. 74(12): 5350–5354.
Britten et al. 1968), Sci. Am. 222(4): 24–31.
Maxam et al. (1977), Proc. Nat'l Acad. Sci. 74(2): 560–564.

*Primary Examiner*—Sidney Marantz
*Attorney, Agent, or Firm*—Pennie & Edmonds

[57] ABSTRACT

This invention provides a method of detecting nucleic acid molecules employing cRNA probes in a pre-electrophoretic hybridization procedure. In addition to detecting the presence of nucleic acids an additional embodiment of the invention permits a determination of the size of said nucleic acids to be made.

15 Claims, 16 Drawing Figures

FIG. 2Aa
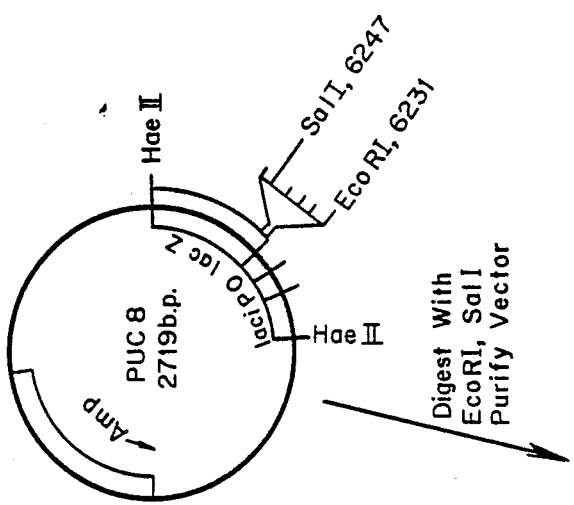
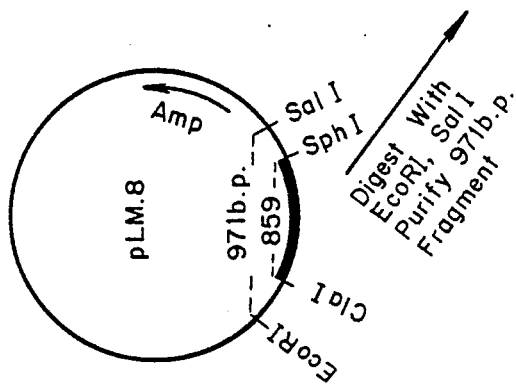

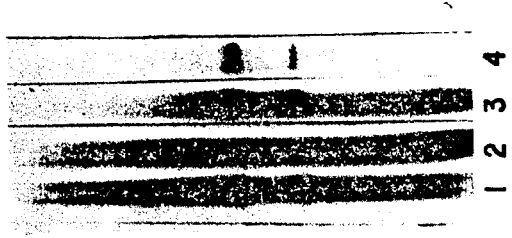
FIG. 6
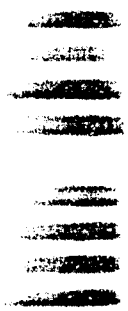
FIG. 5

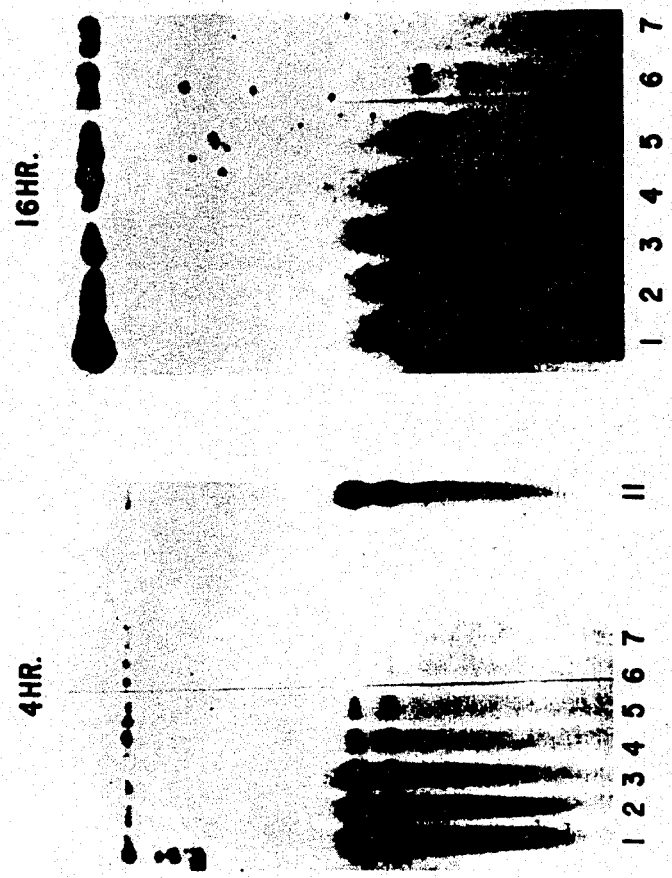

PRE-ELECTROPHORETIC NUCLEIC ACID HYBRIDIZATION

FIELD OF THE INVENTION

This invention relates to the field of diagnostic molecular biology. More specifically this invention provides a method for detecting a specific nucleic acid sequence by pre-electrophoretic hybridization.

BACKGROUND OF THE INVENTION

At physiological temperature and pH, DNA molecules assume the native, duplex form. Intramolecular hydrogen bonds and stacking interactions are responsible for the maintenance of base pairing between complementary DNA strands. If base pairing is disrupted (e.g. through thermal melting) the native molecule assumes a randomly coiled, single-stranded form. Once denatured, the capacity for the DNA to reanneal at complementary regions depends upon nucleotide sequence homology. The localization of specific DNA sequences is achieved through hybridization of a labeled complementary probe to the DNA sequence of interest, under conditions which favor localized duplex formation. Restriction endonuclease cleavage of large duplex DNAs into small fragments which can be sized by gel electrophoresis, in coordination with hybridization of probes to their complementary DNA sequences within these fragments, has enabled the mapping, sizing, and detection of specific genes within these subregions.

The localization of specific DNA sequences within restriction fragments is accomplished usually through a process known as Southern Transfer (Southern, E. M., *J. Mol. Biol.* 98:503-517 (1975)). In this technique DNA fragments are electrophoresed on an agarose gel, denatured, and transferred to a nitrocellulose filter. The immobilized DNA is then probed with $^{32}$P-labeled DNA or RNA. Autoradiography is employed to visualize DNA fragments to which the hybridized probe is complementary. Since the nitrocellulose is a porous, rigid support for DNA, the rate of hybridization between the probe and the DNA sequence is slow since only one component of the reaction is allowed to search for its complement. Furthermore, because $^{32}$P has an affinity for nitrocellulose, the filter must be washed thoroughly to rid it of any loosely bound probe in an attempt to reduce background noise.

BRIEF DESCRIPTION OF THE INVENTION

In one of its embodiments the subject invention employs in vitro synthesized and labeled complementary RNA to the DNA to be tested, as a probe for hybridization. Unlike hybridization methods which require the immobilization of test DNA on a solid support, pre-electrophoretic DNA-RNA hybridization involves hybridization of cRNA to its complement in solution, and in the presence of formamide. This technique has two advantages over Southern Transfer in that:

1. it is faster and 2. it is more sensitive. These advantages arise from the fact that liquid hybridization permits both reactants freedom of movement to base pair with one another thus both the speed of reaction and the sensitivity of detection are both beneficiated. Furthermore, since the laborious washing steps associated with the Southern Transfer are avoided, the entire procedure can be performed considerably more rapidly.

This technique can be performed to identify foreign, infectious DNA, whether free or integrated into the host chromosome, or to detect restriction fragment polymorphisms. The technique is able to detect picogram quantities of DNA in less than 24 hours, while the current Southern Transfer technique takes 2-10 days to detect similar levels of material.

Briefly, the invention provides a method for the detection of nucleic acids by hybridization the improvement comprising: providing a discrete RNA probe; contacting said RNA with the nucleic acid to be detected in a solution under hybridizing conditions; and detecting a hybrid formed after electrophoresis.

In another embodiment the inventor provides a method for sizing DNA comprising hybridizing the DNA to be sized with a cRNA probe of discrete size; subjecting the hybrid to electrophoresis for a sufficient period of time to permit the migration of said hybrid; and comparing the rate of migration of said hybrid with hybrids consisting of said cRNA probe and DNAs of predetermined size.

DETAILED DESCRIPTION OF THE FIGURES

FIG. 5 is an autoradiogram demonstrating the influence of temperature on the formation of PUCLM8 Hind III cRNA/pT24 Bam HI DNA hybrids.

FIG. 6 is an autoradiogram demonstrating the effect of RNAase A treatment of hybridization reactants.

FIG. 7 is an autoradiogram demonstrating the influence of DNA concentration on PUCLM8 Hind III cRNA/pT24 Bam HI—digested DNA hybridization.

Figure 1A:
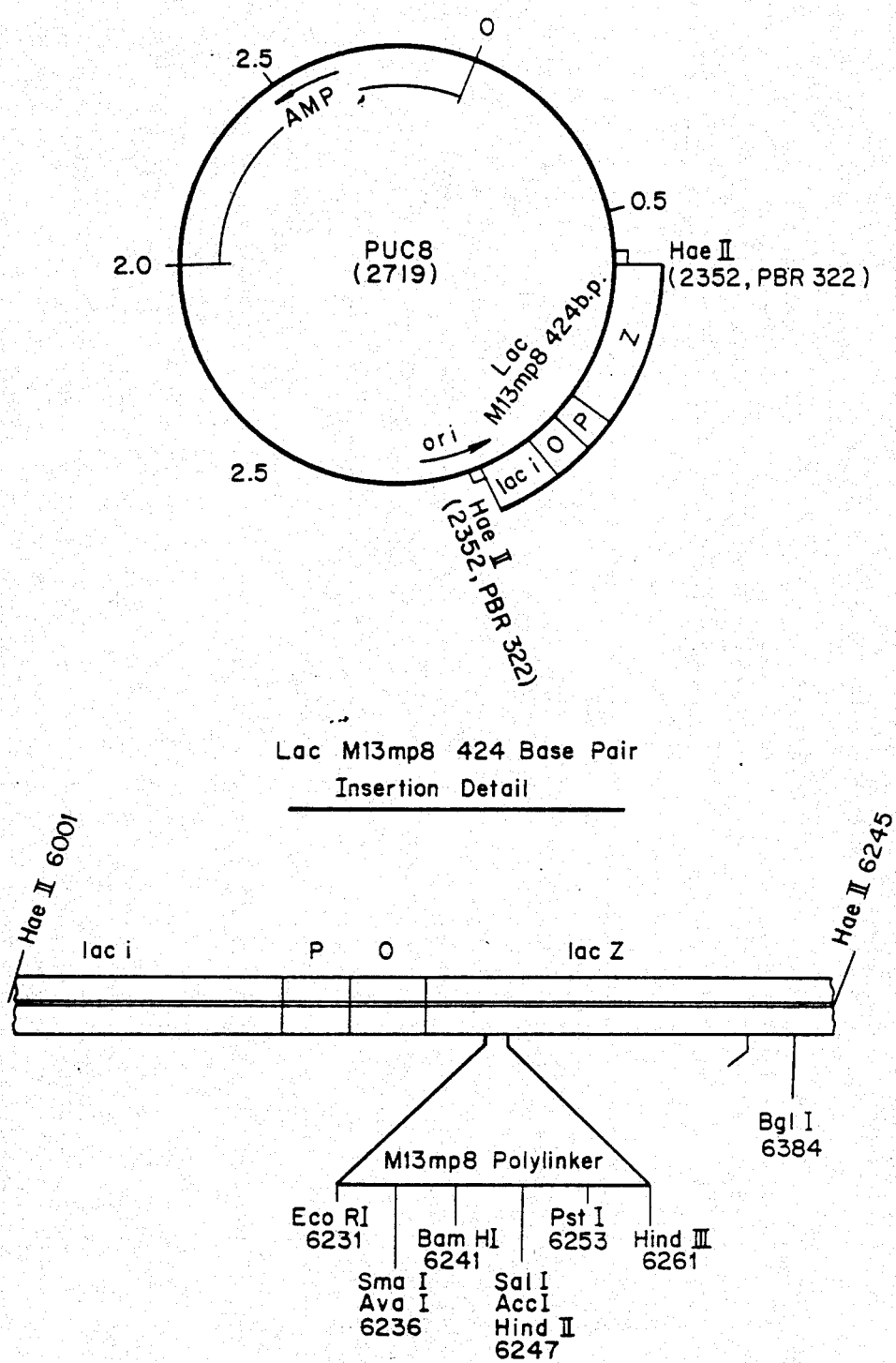
FIG. 1A is a diagramatic representation of the PUC8 plasmid. The lac M13mp8 insert is shown in greater detail.

DETAILED DESCRIPTION OF THE INVENTION cRNA Synthesis

The subject invention contemplates the use of a plasmid containing a strong promoter as a cloning vehicle for test DNA and as a transcription template from which labeled cRNA is synthesized. Any plasmid system containing multiple, unique restriction endonuclease sites available for insertion of test DNA immediately adjacent and 3' of a promotor for which RNA polymerase has a strong affinity is well suited as a transcription template. Some plasmids which contain inserted promoter sequences and allow great flexibility in the choosing of test DNA insertion sites are (1) λ pPL, a vector containing the λ PL promoter (Shimatake and Rosenberg, *Nature* 292:128, (1981)), (2) pSP64 and pSP65, two plasmids constructed to contain a Salmonella SP6 promotor (Melton, D. A.; and P. Krieg, *Nature* 308: 203–206 (1984)) and 3) the PUC plasmids (particularly PUC8 and PUC9) which contain the Lac promoter from M13 (Messing, J. and J. Vieira, *Gene* 19:3, 1982). As exemplified below, the 2.7 Kb PUC8 plasmid may be used as a transcription template and cloning vector. As described in FIG. 1 PUC8 contains a 424 base pair insertion from M13 (6001–6425) which includes the Lac promoter sequence, and multiple, unique restriction sites provided by the M13 polylinker and truncated Lac Z gene sequences. The PUC8 plasmid is publicly available and may be obtained from P.L. Biochemicals.

Alternatively the DNA to be inserted or the plasmid vehicle itself may be modified to include particular endonuclease restriction site by incorporation of adapter oligonucleotides as described by Wu, et al. in U.S. Pat. No. 4,321,365.

It has now been appreciated that in order to generate a specific cRNA probe useful for the practice of the subject process, conditions which: optimize the ability to initiate RNA chain synthesis at the promoter, and terminate synthesis of cRNA at a specific site 3' from the test DNA sequence are required. Parameters such as DNA:RNA Polymerase ratio; initiating nucleotide triphosphate, $^{32}$P-nucleotide and transcription salt KCl concentrations; and temperature of incubation determine whether the cRNA synthesized will be of sufficient specific activity and length, and will be initiated at the Lac promoter. In order to promote the synthesis of cRNA of high specific activity, $^{32}$P CTP is supplied as the sole source of this nucleotide triphosphate to be incorporated into nascent RNA chains. Because it is the limiting nucleotide triphosphate, CTP must be present in transcription reactions in sufficient concentrations so as to prevent premature termination of transcription. Depending on the size and location of the inserted test DNA, a specific site is chosen 3' of the insert where a restriction endonuclease cleaves the DNA, thereby defining a termination point for cRNA synthesis. One particularly useful site of termination of transcription is the 3' restriction site into which the test DNA is originally cloned. If the gene is inserted into the transcription vector by blunt-end ligation, a unique restriction site is chosen within the M13 polylinker sequence immediately flanking the gene as the termination point for RNA synthesis.

If transcription conditions which allow synthesis of RNA initiated at the Amp promoter as well as the Lac promoter are not particularly desirable, transcription from the Amp promoter may be rendered inactive by restricting the template DNA with MboII. This enzyme cuts the plasmid between the RNA polymerase binding site (TATA box) and the DNA sequence conferring the initiation of RNA synthesis, thereby preventing transcription of the Amp gene. MboII does not recognize its cutting sequence anywhere in the region preceding the M13 polylinker DNA in PUC8, hence transcription initiated at the Lac promoter is not terminated prematurely.

After transcription, the cRNA probe is purified from the reactants. The template DNA is degraded by DNAase I so as not to be a competitor during the hybridization of cRNA to its complementary sequence in the test DNA. It was found that, if not sufficiently diluted, the transcription salts inhibit the ability of DNAase to degrade DNA in its prescribed buffer. First, the transcription mixture is precipitated with ethanol in a large volume to eliminate the majority of unincorporated $^{32}$P CTP. Then, the pellet is resuspended in 1 ml. of DNAase buffer 40 ug of DNAase I. This methodology ensures that an enzyme concentration of 40 ug/ml is able to degrade between 200 ng-25 ug of DNA into pieces 40 base pairs or less. The probe is precipitated with 2M LiCl in order to preferentially select single-stranded RNA molecules of great length, and to further eliminate unincorporated nucleotide triphosphates.

Pre-Electrophoretic Hybridization

The purified cRNA is used as a probe for complementary sequences in test DNA under conditions which favor DNA-RNA hybridization. For DNA-RNA hybridization reactions carried out in the presence of 80% formamide, there is a range of temperature which is above the strand separation temperature of duplex DNA and at which the formation of DNA/RNA hybrids is favored. The temperature range which satisfies both criteria is between about 52° to about 60° C. It is, of course, well-recognized that a predictable relationship exists between the percentage of formamide and the temperature required for strand separation of duplex DNA. The relationship being a 0.7° C. change per each 1% formamide. It is thus within the capabilities of a skilled artisan to select a particular formamide-temperature combination for any specific situation.

The efficacy of the subject method is predicated on the recognition that since the helical structure of DNA/RNA hybrids is approximately 30° C. more stable than corresponding DNA/DNA hybrids under formamide hybridization conditions, thus a hybridization temperature range is selected which is above the DNA/DNA strand separation temperature thereby eliminating artifacts generated by the reannealing of reiterated DNA sequences.

Within the above recited temperature range for hybridization in the presence of 80% formamide, the G-C base content of the sequence to be hybridized directly affects the suitability of a specific temperature for the formation of various DNA/RNA hybrids. It is, therefore, preferred to conduct preliminary hybridizations to determine the optimal temperature in specific situations. The results of such hybridizations are illustrated in FIG. 7. The efficiency of hybridization is assayed by electrophoresis on 1% agarose gels and subsequent autoradiography. In such a system a single stranded nucleic acid molecule will migrate slowly through the gel whereas completely double stranded (duplex) nucleic acid will migrate more rapidly, the actual rate being a function of the size of the migrating duplex. The cRNA/DNA hybrid molecules migrate as distinct band, with a mobility in the gel intermediate to that of purely single stranded or completely double stranded nucleic acid.

The mobility of the cRNA/DNA hybrid in the gel is dependent on the single-stranded length of the test DNA molecule and the percentage of double-stranded character contributed by the length of the complementary sequences in the cRNA probe. Non-hybridizing single-stranded sequences within in cRNA probe affects the mobility of the hybrid molecule as well.

It has also now been appreciated that in situations involving cRNA/DNA hybrids where the test DNA is larger than the cRNA probe, the locus of the base complementary in the DNA molecule may affect mobility. That is to say, if the probe hybridizes at a position near the mid-point of the test DNA two-single stranded tails of DNA will result one at each end of the hybrid, whereas if the hybridization takes place at a position distal or proximal to the midpoint only a single strand tail may result. Regardless of the effect of the size of the test DNA or the actual locus of hybridization, it is within the skill of an artisan to establish the specific effect of these parameters by performing hybridization and subsequent electrophoresis of a given cRNA probe with DNAs of predetermined size and for which the relative point of hybridization is known.

With respect to the hybridization phase per se, it should be appreciated that the reannealing of the complementary strand of DNA could (1) displace the cRNA probe by branch migration and/or (2) create a molecule which would migrate very close to that of a double-stranded duplex DNA molecule (reannealed DNA containing an R-loop structure). Hybridization reactions are preferably carried out in RNA probe excess with respect to the DNA sequence to be detected. For a given amount of DNA involved in hybridization with cRNA, it is the concentration of probe which dictates the rate of formation of hybrid molecules. Once a critical excess of cRNA has been attained, subsequent addition of probe to the reaction does not increase the rate of hybridization. At this point of cRNA excess, the amount of DNA available to hybridize determines when the system is saturated. The fraction of cRNA probe which does not hybridize to DNA remains in the reaction mixture, and when electrophoresed, appears as background noise in the lower molecular weight region of the agarose gel. The intensity of this background noise is sufficient enough to obscure the detection of picograms of test DNA. In order to detect picogram quantities of DNA, and to visualize DNA/RNA hybrid bands clearly, hybridization reactions are treated with RNAase A. Background noise is reduced considerably through the degradation of single-stranded cRNA probe by the enzyme. RNAase A does not degrade the base pairing region of the cRNA/DNA hybrid appreciably. In any transcription system, sequences which are not complementary to the gene for which the cRNA is a probe, constitute a certain fraction of the total length of the probe which is unable to hybridize to test DNA. The "leader sequence," or the region within the probe, starting at the initiation site of RNA synthesis, and terminating at 5' end of the cloned gene (75 bases in the PUCLM8 plasmid, see FIG. 1) is an example of such a heterologous sequence. Furthermore, an additional region of nonhomology can be created if the restriction site for the termination of RNA synthesis is chosen in the polylinker sequence of the plasmid, downstream from the 3' end of the gene. As mentioned above, these sequences can be visualized as single stranded RNA "tails" in the DNA/RNA hybrid molecule which add more single stranded character to the mobility of the hybrid. RNAase A treatment of the hybrids digests the single stranded tails thus reducing this source of variability without disrupting the integrity of the base-pairing region.

Finally, electrophoresis conditions are established in order to preserve the integrity of cRNA/DNA hybrids and not to permit reannealing of DNA; thus, the advantages accruing from the liquid hybridizations in formamide are preserved during the electrophoresis procedure. For example, gels run at 200 volts are heated to temperatures of about 50° C.; DNA molecules suspended in the running buffer, which contains a high percentage of formamide, cannot reanneal at this temperature. Gels are electrophoresed for a period of time sufficient to separate the non-hybridizing single-stranded DNA molecules form the cRNA/DNA hybrid structures. Hence, when the electrophoresis is complete and the gel cools to temperatures at which DNA may reanneal, DNA/DNA hybrids do not form since the complementary strands have been immobilized and physically separated by charge.

Materials and Methods

Enzymes and Nucleotides

Restriction endonucleases and T4 DNA ligase were obtained from New England Bio Labs, Beverly, Mass. Alkaline phosphatase was obtained from Sigma Chemical Co., St. Louis, Mo. These enzymes were applied as recommended by the supplier. RNA polymerase holoenzyme, RNAase-free Bovine Pancreatic DNAase I, and RNAase A were all obtained from Worthington Diagnostics, Inc., Freehold, N.J. Alpha $^{32}$P CTP (410 Ci/mmole) was purchased from Amersham.

Plasmids

The plasmid used as a cloning vehicle and transcription template was the 2719 b.p. PUC8 plasmid (Messing and Vieira, *Gene*, 19:3, 1982) obtained from PL Biochemicals Piscataway, N.J. The host for the plasmid is the *E. coli* K-12 strain JM103 (thi,lac,pro), StrA, supE, endA,/sbcB, hsdR, proAB, lacI$^q$, Z Δ, M15). Host cells were transformed with plasmid using calcium chloride treatment (Cohen et al., *Proc. Nat'l Acad. Sci. USA* 69:2110, (1973). Cells were streaked on plates containing YT media, 50 ul of 5 mg/ml ampicillin and 50 ul of 2% Xgal. 10 ul of 100 mM IPTG was added as an inducer for the strain. The plasmid was purified from large preparations by centrifugation to equilibrium in cesium chloride-ethidium bromide gradients (Maniatis, T., et al. Molecular Cloning: A Laboratory Manual, Cold Spring Harbor Laboratory, (1982).

The relevant features of PUC8 are illustrated in FIG. 1A; the lac insert is shown in greater detail.

Figure 1B:
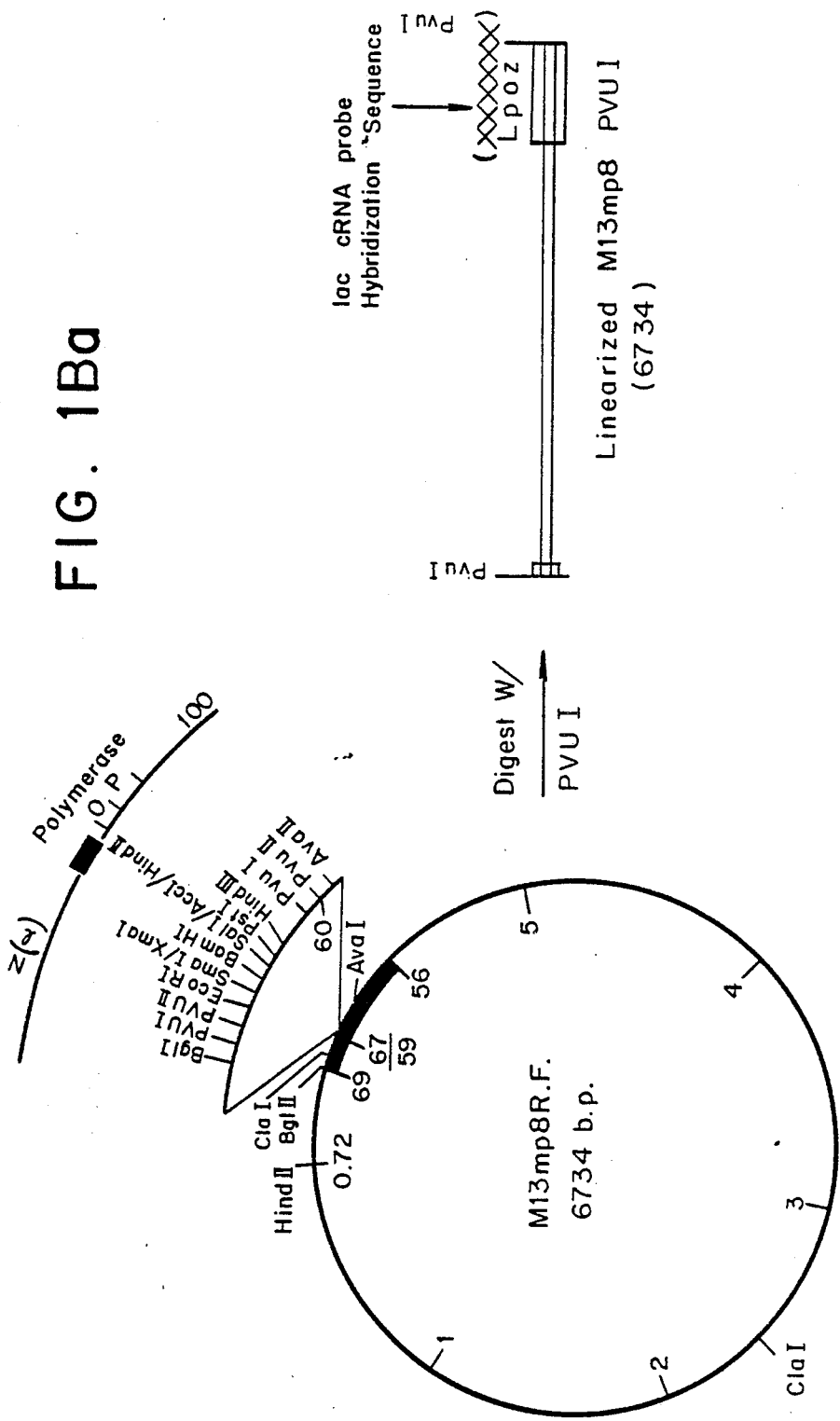
FIG. 1B is a diagramatic representation of vector M13Mp8 and pT24.
Figure 1B:
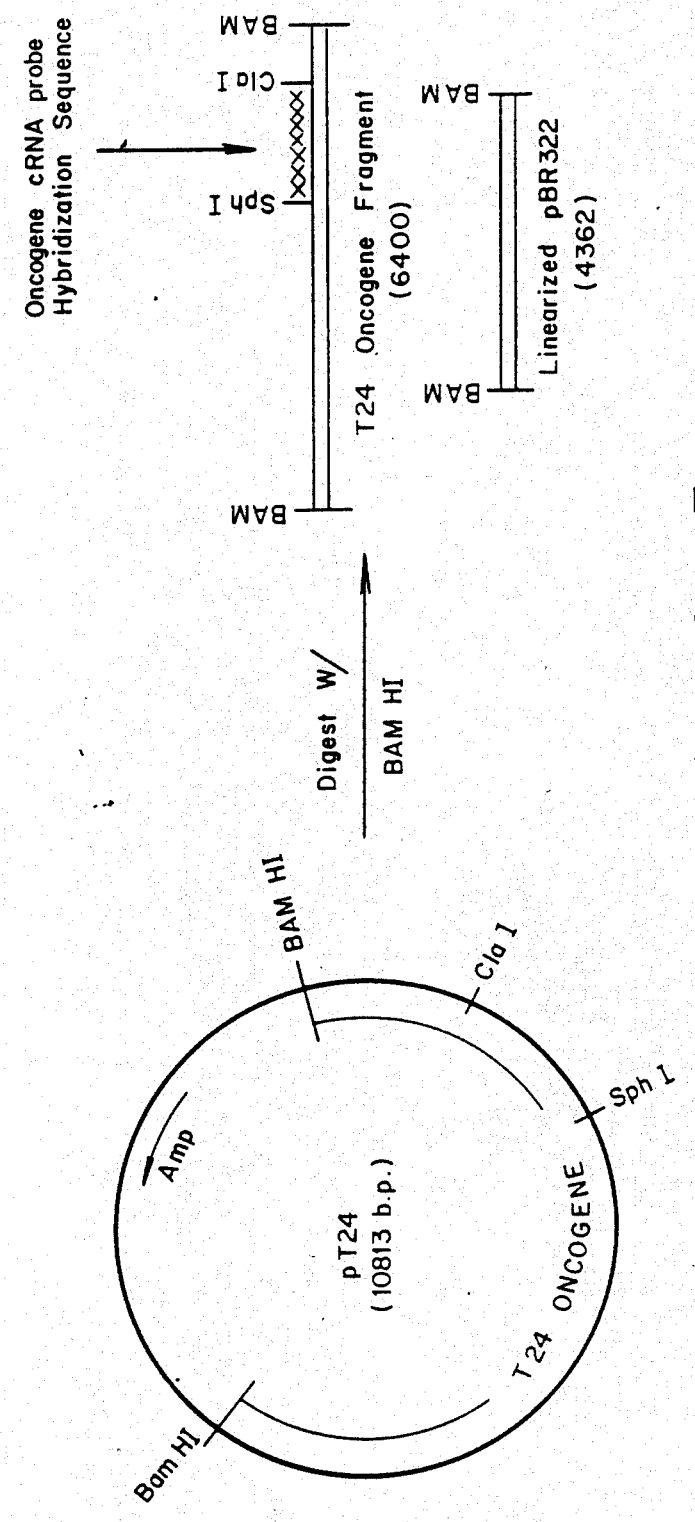
Figure 1C:
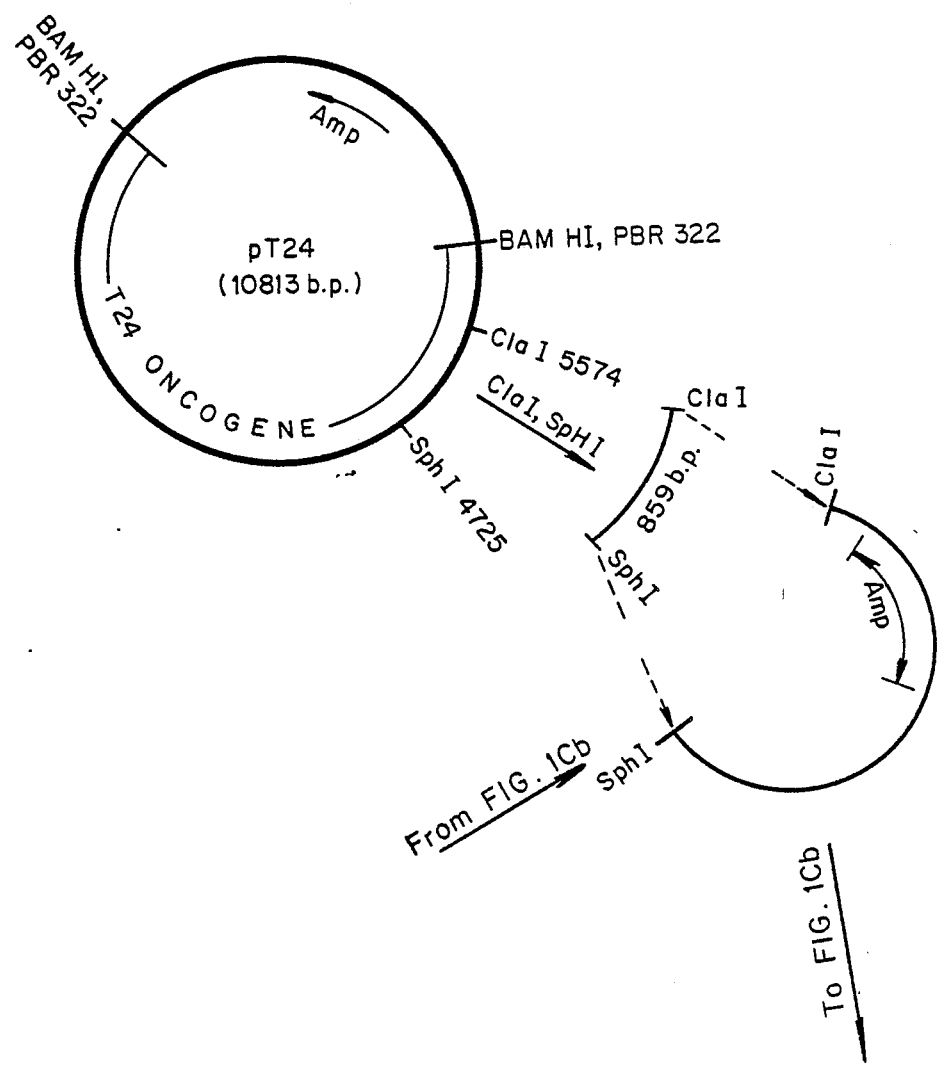
FIG. 1C illustrates the steps in the construction of plasmid pLM.8.
Figure 1C:
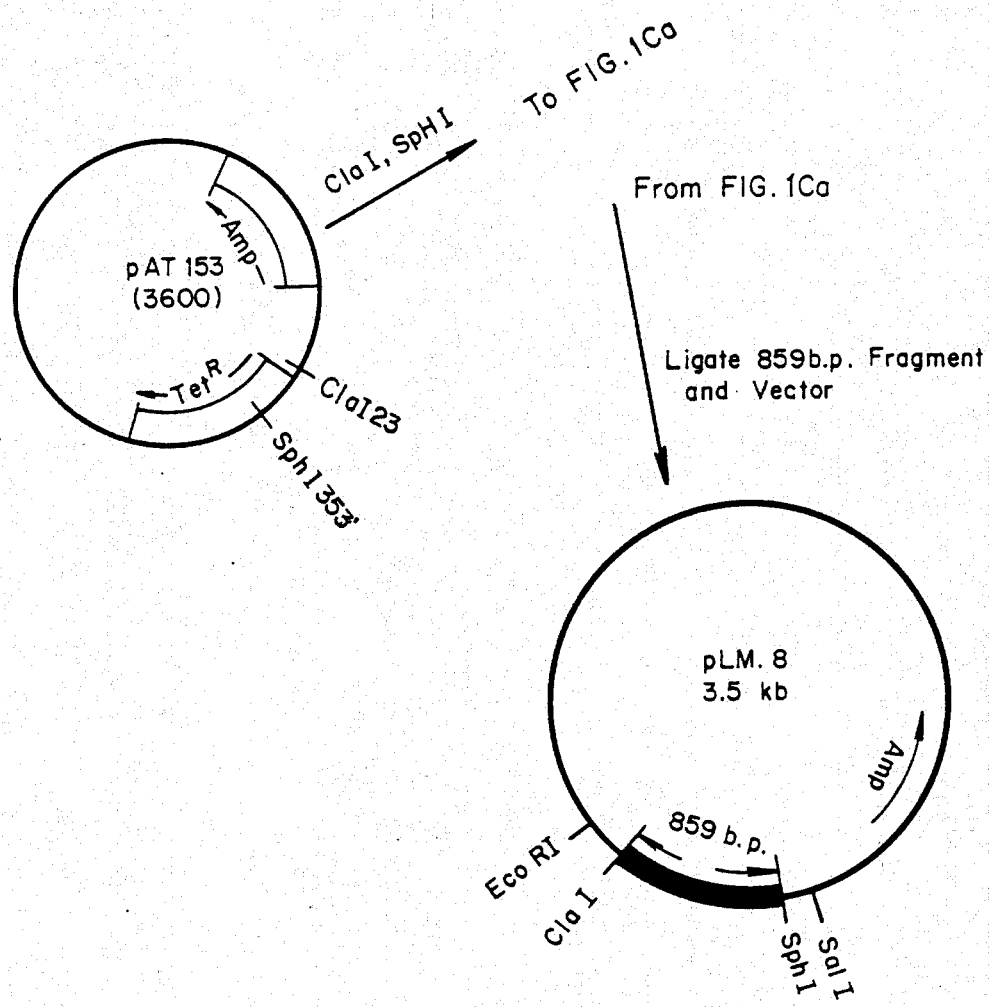

FIGS. 1B and 1C illustrate other plasmids employed to demonstrate the subject invention in the example which follows. These plasmids include the replicative form of M13mp8 which contains a lac operon insert, pT24 a plasmid containing the T24 oncogene pLM.8 a 3.5 Kb plasmid derived from plasmid pAT153 and containing an 859 b.p. insert of T24 oncogene DNA obtained from plasmid pT24 as detailed in FIG. 1C. pT24 described by Goldfarb, M et al. *Nature* 296:404-408 (1982) is available from the ATCC (American Type Culture Collection 12301 Parklawn Drive, Rockville, Md.) under accession number 41000. The plasmid PLM.8 was also deposited in the ATCC under accession number 39604. The virus M13mp8 may be obtained from BRL, Bethesda, MD.

Insertion of T24 Oncogene Fragment into PUC8

Figure 2A:
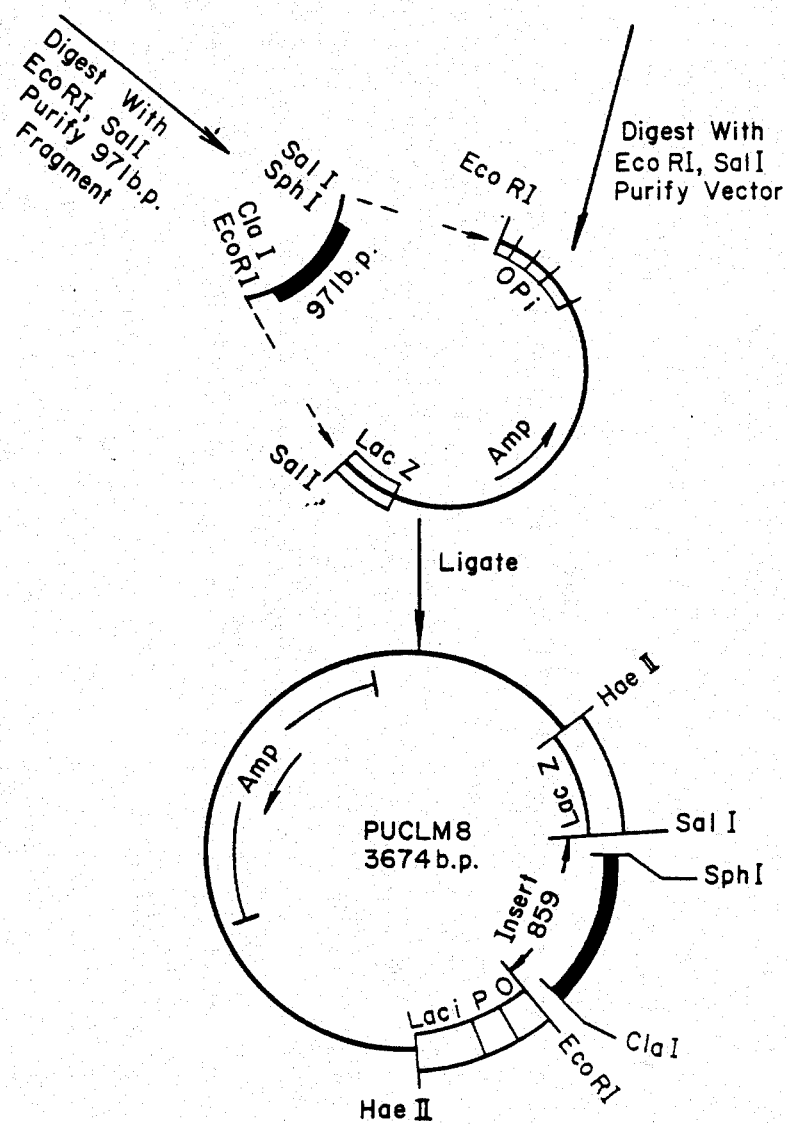
FIG. 2A illustrates the steps in the construction of plasmid PUCLM8.
Figure 2B:
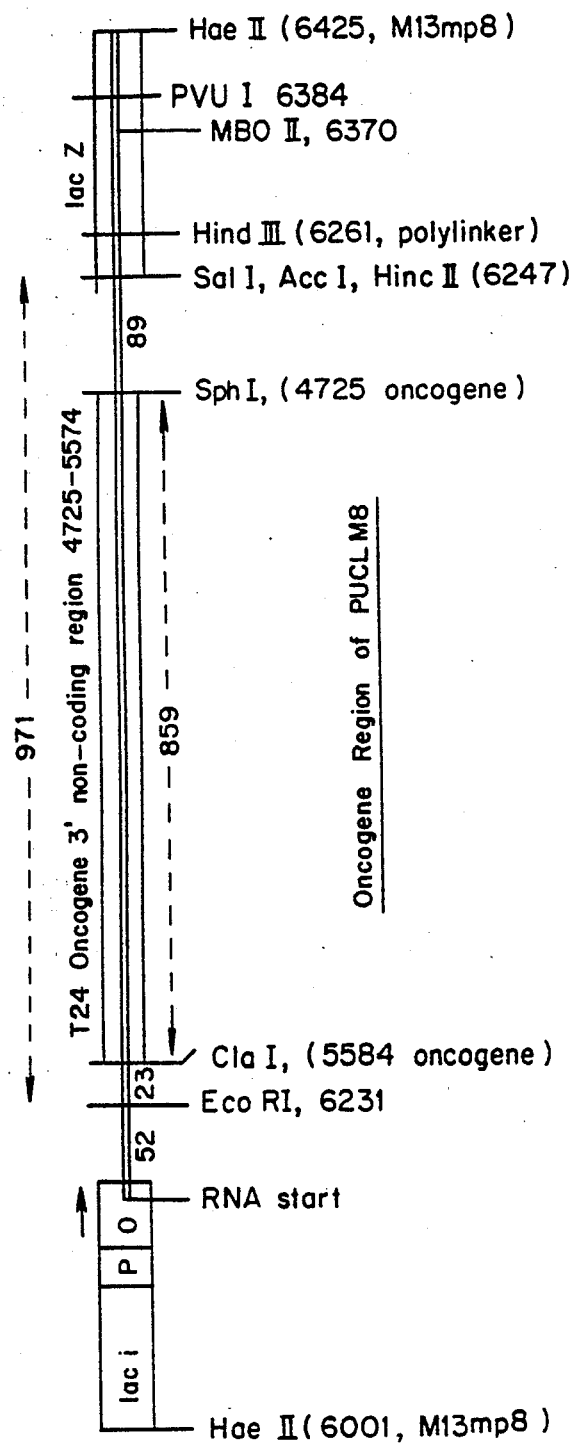
FIG. 2B is a diagramatic illustration in greater detail of the onocogene region of PUCLM8.

The recombinant plasmid PUCLM8 (3674 b.p.) was constructed by the insertion of a fragment containing an 859 base pair sequence from the 3' non-coding region of the T24 onocogene (4725-5584) into the PUC8 vector at a site immediately 3' to the Lac promoter sequence. The onocogene sequence was isolated from a subclone of pT24 in which an 859 base pair Cla1-Sph1 fragment from pT24 was inserted into a pAT153 vector as described above and illustrated in FIG. 1C. The subclone, PLM.8, was restricted with EcoR1 and Sal1 enzymes. A 971 base pair fragment was purified by agarose gel electrophoresis and electroelution, followed by extraction with phenol/chloroform and precipitation with ethanol (Maniatis, T., et al, supra (1982)). This Eco R1-Sal1 fragment contained 23 base pairs of DNA from PAT153 5′ of the ClaI site delimiting the 5′ end of the onocogene sequence, and 89 base pairs 3′ of the Sph1 site delimiting the 3′ end of the gene. The PUC8-oncogene fragment recombinant was constructed as follows: PUC8 was restricted with EcoR1 and Sal1. After complete digestion, the enzymes were heat-killed for 5 minutes at 68° C. The vector was then treated with 0.01 unit of alkaline phosphatase (as prescribed by the suppliers, Sigma Chemical Co.). The phosphatase was heat-killed and the vector was extracted and precipitated as indicated previously. The vector and the 971 fragment were treated with 0.1 unit of T4 DNA ligase, and incubated overnight at 15° C. Ligation reactions were assayed on 1% agarose minigels. 500 ng of ligated DNA were used to transform JM103 cells. The cells were streaked on YT/Amp/Xgal plates and were induced with IPTG. White colonies were selected and plated anew. The plasmid was amplified, and purified by centrifugation to equilibrium in "CsCl"-EtBr gradients as indicated above. The plasmid was finally extracted with phenol/chloroform and precipitated with ethanol in order to obtain an $A_{260}/A_{280}$ ratio of 2/1. A diagramatic representation of the construction is provided in FIG. 2A. The detail of the Hae II cassette is given in FIG. 2B.

Preparation of Transcription Template DNA

The appropriate plasmid was restricted with a selected endonuclease, such as Pvu I or Hind III, extracted with phenol/chloroform and precipitated with ethanol. The points of restriction endonuclease cleavage, thereby defined the termination sites for the synthesis of the cRNA.

Transcription 2 ug of restricted plasmid were incubated at 30° C. for 10 minutes with 0.125-0.5 unit of $E.$ $coli$ RNA polymerase holoenzyme in a buffer containing 40 mM Tris/HCl (pH 8.0), 4 m 4 $MgCl_2$, 10 mM 2-Mercaptoethanol, 120 mM KCl and 5% glycerol (Chamberlin et al., $Meth.$ $in$ $Enzymol$ 101:540-68 (1983)), and 2.7 mM, 1.4 mM, 1.1 mM ATP, UTP, GTP, respectively. RNA polymerase was diluted in 81RP buffer as described by Chamberlin et al., (J. Biol. Chem., 254(20): 10061-69 (1979)) prior to addition. Transcription was initiated upon addition of varying concentrations of alpha $^{32}P$ CTP, 410Ci/mmole. Reaction volumes were 50 μl. The transcription was carried out in a Lauda recirculating/regulating bath at 30° C. for 30 minutes. Reactions were terminated on ice, whereupon the samples were diluted 1/10 with distilled $H_2O$. The reactions were immediately extracted with phenol/chloroform and precipitated with 3 volumes of ethanol in the presence of 0.15M NaOAc and 10 μg/ml tRNA carrier, and pellets were resuspended in 100 μl of distilled $H_2$. Percentage incorporation and specific activity data of transcription reactions were assayed by TCA precipitation; cRNAs were sized on 5% Acrylamide/8M urea gels (15.9×30 cm, 0.8 mm in thickness). cRNAs used as probes for hybridization generally had a specific activity between 0.6-2.0×$10^{10}$ dpm/nmol.

Purification of cRNA Probe

The transcription reaction was treated with Bovine Pancreatic DNAase I (RNAase-Free, Worthington Diagnostics) in the presence of 50 mM NaOAc, 10 mM $MgCl_2$ and, 1 mM EDTA adjustud to a pH of 6.0 at a concentration of 40 μg/ml. The total reaction volume of 1 ml was incubated at 37° C. for 30 minutes, and terminated on ice. The enzyme was removed by extraction with phenol/chloroform and the cRNA was precipitated with 3 volumes of ethanol. The pellet was dissolved with 100 μl of distilled $H_2O$ and mixed with an equal volume of 4M LiCl (Harris, et al., $Biochemistry$ 17:3250-56(1978)). LiCl precipitation was carried out for 6 hours at 0° C. in the presence of 200 μg/ml single-stranded RNA carrier. RNA was pelleted by centrifugation at 10,000 r.p.m. for 10 minutes. The pellet was resuspended in a volume of 200 μl of distilled $H_2O$, precipitated with ethanol in the presence of 0.15M "NaOAc", and washed briefly with 70% ethanol. The cRNA probe was finally resuspended in distilled $H_2O$ at a concentration of 300 pg/μl (approximately $1 \times 10^6$ dpm/μl). The probe can be stored at −20° C. for 2 weeks before appreciable $^{32}P$-suicide occurs.

Hybridization

Either $^{32}PCTP$-labeled PvuI-terminated PUC8 cRNA or Hind III-Terminated PUCLM.8 cRNA (approximately 1 ng, 3-4 x $10^6$ dpm), desired amounts of respective test DNAs, M13Mp8 cleaved with PvuI or pT24 cleaved Bam H1 (10 pg-1 ng), and 10 μg of carrier tRNA were placed in a sterile Eppindorf centrifuge tube. The contents were brought to a volume of 50 μl with 0.3M NaOAc, and precipitated with 3 volumes of ethanol at −70° C. for 20 minutes. The material was centrifuged for 10 minutes at 10,000 r.p.m. at 4° C. The pellets were washed with 70% ethanol and dried by vacuum centrifugation. The pellets were resuspended in 10 μl of a buffer containing 40 mM PIPES (pH 6.4), 0.1 mM EDTA (pH 8.0), 0.4 M NaCl, and 80% formamide (Berk and Sharp, $Cell$ 12:721, (1977)). The formamide used was of reagent grade purity, recrystallized to a conductivity of 1-2 μohm. Samples were sealed with Parafilm, denatured by immersion in a 72° C. water bath for 15 minutes, and transferred to a water bath at an appropriate temperature (52°-60° C.). Hybridizations were conducted for 3 hours, and were terminated on ice.

RNAase A Treatment of Hybrids

The hybrids were treated with 5-50 μg/ml RNAase A in the presence of 0.2M NaCl and 40% Formamide for 30 minutes at 22° C. (i.e. the 10 μl hybridization reaction volume was brought up to a volume of 20 μl upon addition of 9 μl of distilled $H_2O$ and 1 μl of 100 μg/ml-500 μg/ml RNAase A).

The samples were brought to 36 μl, final volume upon addition of 10 μl of TBE buffer and 6 l of loading buffer III (0.25% bromophenol blue, 0.25% xylene cyanol, 30% glycerol in $H_2O$ (Maniatis, T, et al. Supra (1982)).

Electrophoresis and Autoradiography

Samples were loaded onto 150 ml, 13-well, 1% agarose gels containing 0.05 μg/ml ethidium bromide in TBE buffer. Alternatively, the samples were run on gels heated to temperatures at, or near the temperature of hybridization. When in a High Resolution Electrophoresis apparatus equipped with a gel bed heating module; a voltage of 80 Volts was employed. The gels were dried on Whatman 3 mm paper (double thickness) in a slab drier under vacuum for 2-3 hours (overdrying leads to fragmentation of gel), and autoradiographed with Kodak X-ray film in a casette with an intensifiying screen at −70° C. for 1-16 hours.

EXAMPLE I

This example illustrates the hybridization assay employing as a probe cRNA for the lac Z gene. In the example a portion of the lac sequence of phage M13 was used for the synthesis of the cRNA probe.

The transcription template DNA was the PUC8 plasmid restricted with the enzyme PvuI. PvuI cleavage of PUC8 produced two fragments. "Run-off" cRNA was sythesized from the 1700 base pair fragment containing the Lac promotor. CTP concentrations between 3-10 uM were adequate to ensure the production of full length run-off transcripts. The hybridizing DNA was M13mp8 digested with PvuI. PUC8 PvuI cRNA/M13mp8 PvuI DNA hybridization reactions were conducted for 3 hours at 52° C. The DNA/RNA hybrid molecule appears as a single band migrating between the double stranded and single stranded forms of M13mp8 PvuI-digested DNA. When LiCl-precipitated cRNA was employed as probe, the background noise was decreased considerably since a greater percentage of the cRNA pool was available to hybridize, while smaller RNAs were excluded (FIG. 3).

Figure 3:
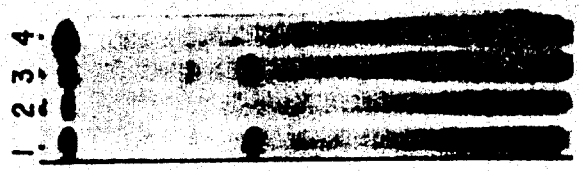
FIG. 3 is an autoradiogram demonstrating the effect of LiCl precipitated PUC8 PvuI cRNA in hydridization reactions.

With reference to FIG. 3, it can be shown that LiCl precipitation of PUC8 PvuI cRNA selects larger RNAs from the total transcript pool which comprise a higher percentage of RNAs available for hybridization. Lane 1: 100 pg of M13mp8 PvuI-digested test DNA and $4 \times 10^6$ dpm PUC8 PvuI cRNA which had been treated with DNAase I and precipitated with 2M LiCl for 6 hours, 0° C., in the presence of 200 μg/ml single-stranded RNA carrier were hybridized. Lane 2: Endogenous hybridization of $4 \times 10^6$ dpm LiCl-precipitated, DNAase-treated cRNA without test DNA was carried out. Lane 3: 100 pg of test DNA and $4 \times 10^6$ dpm DNAase I-treated cRNA was hybridized without test DNA. All hybridization were carried out for 5 hours at 52° C. Samples were electrophoresed on a 150 ml, 1% Agarose gel-TBE for 2 hours at 200 volts. The autoradiogram was exposed for 4 hours.

EXAMPLE II

This example illustrates the preparation and use of cRNA probes for the human T24 onocogene. This example involved the synthesis of a cRNA probe from the PUC8 vector containing a portion of the T24 oncogene. A transcription plasmid, PUCLM8 (3674 b.p.) was constructed by inserting an 859 base pair restriction fragment from the 3' non-coding region of the T24 oncogene (seq. 4725-5584) into the PUC8 vector immediately downstream form the Lac promoter sequence. cRNA generated from transcription of PUCLM8 is used as a probe for the 859 base pair sequence present within a non-homologous plasmid, pT24 (Goldfarb et al., supra (1982). The 859 b.p. oncogene fragment is an extremely useful probe in hybridization studies since nick-translated fragment has been shown to detect restriction fragment polymorphisms when used as a DNA probe in Southern hybridizations vs. total human DNA digested with PstI, TaqI, and Bam HI, respectively.

α $^{32}$P CTP cRNA synthesized from a PUCLM8 template digested with Hind III was used as a probe for the oncogene fragment located within a 6459 base pair restriction fragment generated by a Bam HI digest of the pT24 plasmid. In addition to producing an oncogene containing fragment, Bam HI cleavage generates a 4362 base pair fragment containing pBR322 sequences, the vector into which the oncogene is originally inserted. cRNAs synthesized from the Hind III-restricted transcription vector originate from initiation events at the Amp promoter as well as from the Lac promoter. These subpopulations of cRNA are complementary to a fraction of pBR322 and the T24 oncogene, respectively.

[A]Optimizing Transcript Length

Figure 4:
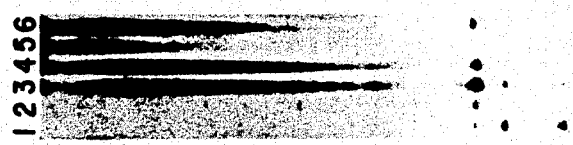
FIG. 4 is an autoradiogram demonstrating the influence of concentration of alpha $^{32}$P CTP on the synthesis of cRNA from PUCLM8 Hind III-digested DNA.

Full length, Lac promoter-initiated cRNA synthesized form Hind III-digested PUCLM8 template is 1037 bases. The transcript contains an 859 base sequence corresponding to the probe for the human T24 oncogene and is flanked by sequences which are unable to hybridize with the oncogene (75 bases 3' and 103 bases 5' to the sites of insertion). For a given template DNA:RNA polymerase ratio, the concentration of limiting nucleotide triphosphate, alpha $^{32}$P-CTP, should be optimized in order to prevent premature termination of transcription. Concentrations of 0.1,1, and 3 μM alpha $^{32}$P-CTP are insufficient to allow the synthesis of full length transcripts, while concentrations between 10-30 μM are adequate (FIG. 4). FIG. 4 illustrates the influence of concentration of alpha $^{32}$P-CTP on the synthesis of cRNA form PUCLM8 Hind III-digested DNA. Transcription reactions were conducted as indicated in the detailed descriptions of the invention in the presence of 0.5 unit RNA polymerase holoenzyme, and varying concentrations of alpha $^{32}$P-CTP. Transcripts were extracted with phenol/chloroform and precipitated with ethanol in the presence of 0.3M NaOAc. $1 \times 10^6$ dpm of cRNA was analyzed on a 5% Acrylamide-TBE/8M Urea denaturing gel. The samples were electrophoresed at 500 volts for 3 hrs. The autoradiogram above is a 20 min. exposure. Track 1: Transcription was conducted in the presence of 0.1 μM alpha alpha$^{32}$P CTP, Track 2: 1 μM alpha $^{32}$P CTP, Track 3: 3 μM alpha $^{32}$P CTP, Track 4: 10 μM alpha $^{32}$P CTP, Track 5: 30 μM CTP (3 μM alpha $^{32}$P CTP, 27 μM CTP), Track 6: 100 μM CTP (5 μM alpha $^{32}$P CTP, 95 μM CTP).

[B]Optimizing the Temperature of Hybridization

Autoradiograms from agarose-gel electrophoresed hybridization reactions indicated that the cRNA initiated at the Lac promoter hybridized to the T24 oncogene DNA fragment, and that cRNA initiated at the Amp promotor hybridized to the pBR322 Bam HI fragment, at every temperature studied between 47°-59° C. (FIG. 5). cRNA/oncogene hybrids were formed more readily and were more stable than cRNA/pBR322 hybrids when reactions are conducted at 59° C. in 80% Formamide/40 mM PIPES/0.4M NaCl. While the signal intensity for the cRNA/oncogene hybrid remained constant over the temperature range, there was a reduction in signal intensity for the cRNA/pBR322 hybrid at 59° C. Since the oncogene sequence to which the RNA probe is complementary is enriched in G, C bases, cRNA-oncogene hybridization was optimal at temperatures at which cRNA-pBR322 hybridization was not. FIG. 5 illustrates the influence of temperature on the formation of PUCLM8 Hind III cRNA/pT24 Bam HI DNA hybrids. 1 ng of pT24 Bam HI-digested DNA and $5 \times 10^6$ dpm PUCLM8 Hind III cRNA were hybridized in a buffer containing 80% formamide, 40 mM PIPES, 0.4M NaCl for 3 hours at temperatures varying 3° C. over a 47°-59° C. range. Hybrids were electrophoresed on a 150 ml., 1% Agarose gel for 2 hours at 200 volts in TBE buffer. The autoradiogram above is a 15 minute exposure. The two bands visualized are cRNA/DNA hybrids. The upper band corresponds to the PUCLM8 Hind III plac cRNA/T24 oncogene molecules and the lower band represents PUCLM8 Amp cRNA/linearized pBR322 (Bam HI) hybrid molecules. The first 5 lanes are numbered according to the temperature at which cRNA and test DNA were hybridized. The last 5 lanes are hybridization reactions conducted without test DNA, under the same temperature requirements. At hybridization conditions of low stringency (47°–53° C.) both cRNA/oncogene and cRNA/pBR322 hybrids formed readily. However, under more stringent conditions (59° C.), the formation and stability of cRNA/pBR322 hybrids was greatly reduced, while cRNA/oncogene hybrids remained intact. cRNA/oncogene hybrid stability was a consequence of the G-C, C-richness of the base-pairing sequence moiety of the hybrid. Background noise was also reduced in cRNA/test DNA and cRNA control hybridizations conducted at 59° C.

[C] Reduction of Background Noise Through RNAase A Treatment

When cRNA-DNA hybridization reactions are treated with the enzyme RNAase A, unhybridized single stranded cRNA probe is degraded while the cRNA/DNA hybrid molecules remain intact. The enzyme also digests the single stranded regions of unhybridized cRNA within the hybrid molecule arising from the inclusion of plasmid sequences in the cRNA which flank the hybridizing sequence moiety, thereby increasing the sharpness of the signal (FIG. 6). The use of RNAase A enables the detection of low levels of DNA which were previously inaccessible.

FIG. 6 shows that RNAase a treatment of hybridization reactions degrades unhybridized single-stranded cRNA without disrupting the integrity of the cRNA/DNA hybrid molecule.

LiCl precipitated PUCLM8 Hind III cRNA-pT24 Bam HI DNA hybridization reactions were conducted at 59° C. for 3 hours in the presence of 80% formamide, 40 mM PIPES, and 0.4M NaCl. Reactions were electrophoresed on a 15 ml, 1% Agarose gel for 2 hours at 200 volts in TBE buffer. The autoradiogram above is a 2 hour exposure. Lane 1: 100 pg of pT24 Bam HI-digested DNA was hybridized to $4 \times 10^6$ dpm DNAase-treated, LiCl-precipitated PUCLM8 Hind III cRNA. Lane 2: LiCl-precipitated cRNA was exposed to hybridization conditions in the absence of test DNA. Lane 3: 100 pg of pT24 Bam HI-digested DNA was hybridized to $4 \times 10^6$ dpm DNAase-Treated, LiCl-precipitated cRNA, as in Lane 1, but 20 µl of TBE buffer was added prior to electrophoresis. Lane 4: A 100 pg hybridization reaction was treated with 5 µg/ml RNAase A in a volume of 20 µl in the presence of 0.2M NaCl and 40% Formamide, for 30 minutes at 22° C. 10 µl of TBE buffer were added prior to electrophoresis.

TBE buffer treatment served to the solubilize cRNA more thoroughly and produce a better signal to noise ratio. RNAase A treatment digested unhybridized cRNA probe as well as single-stranded regions of unhybridized cRNA within the hybrid molecule thereby increasing the sharpness of the signal.

[D] Amount of DNA Detected

Experiments involving the hybridization of LiCl-precipitated, DNAase-treated cRNA probe to the T24 oncogene within a recombinant plasmid were conducted at the optimal temperature with decreasing amounts of DNA at a given cRNA probe concentration. It was shown that pre-electrophoretic DNA/RNA hybridization was capable of detecting 1 picogram of DNA (FIG. 7). A band which represents hybridization of 10 pg of DNA with cRNA probe is clearly visualized by autoradiography in 4 hours, while 1 pg is visualized in 8–16 hours. With reference to FIG. 7 influence of DNA concentration can be seen on PUCLM8 Hind III cRNA-pT24 Bam HI-digested DNA hybridizations. $5 \times 10^6$ dpm of DNAase-treated, LiCl-precipitated PUCLM8 Hind III cRNA was hybridized to varying concentrations of pT24 Bam HI-digested DNA at 59° C. for 3 hours in the presence of 80% formamide, 40 mM PIPES, and 0.4M NaCl. All hybridization reactions were treated with 500 µg/ml RNAase A in a volume of 20 µl for 30 min. at 22° C., in the presence of 40% formamide and 0.2M NaCl. Samples were brought to a volume of 36 µl with 10 µl TBE buffer and 6x loading buffer. Samples were electrophoresed on a 150 ml, 1% Agarose gel for 2 hours at 200 volts. The autoradiogram above was exposed for 5 hours at −70° C. with an intensifying screen. Lanes 1–6 contain 1 ng, 300 pg, 100 pg, 30 pg, 10 pg, and 1 pg of pT24 Bam HI-digested test DNA, respectively. Lane 7 is a hybridization control reaction containing $5 \times 10^6$ dpm cRNA without test DNA. Lane 11 is a hybridization reaction containing 100 pg of pT24 Bam HI-digested DNA and $5 \times 10^6$ dpm DNAase-treated, LiCl-precipitated PUCLM8 Hind III cRNA prepared 2 weeks prior to its use in the experiment. Efficient degradation of unhybridized cRNA by RNAase A treatment of samples has enabled the visualization of 1 pg of test DNA (Lane 6). A comparison between hybridization reactions which employed 2 week-old cRNA vs. freshly-prepared cRNA (Lane 11 vs Lane 3) 0 demonstrates that there is no loss of band sharpness or added background created when 2-week old RNA is used as probe. Hence, cRNA probes can be stored at −20° C. for at least 2 weeks without great risk of degradation through $^{32}P$-suicide.

EXAMPLE III

This example illustrates the detection of the T24 oncogene within human genomic DNA digests.

Since it has been shown in Southern Transfer/Hybridization studies that the 859 base pair oncogene fragment is able to detect restriction fragment polymorphisms in total human DNA digested with Bam HI, TaqI, and PstI, the detection efficiency of a cRNA synthesized from PUCLM8 was tested for the detection of polymorphisms through pre-electrophoretic DNA-RNA hybridization. The amount of oncogene sequence within a restriction fragment of human DNA is on the order of magnitude detectable by the subject invention. Data from hybridization experiments employing cRNA synthesized from a PUCLM8 Hind III-digested template as a probe for DNA sequences within restriction fragments generated by complete digestion of total human DNA with the enzymes Bam HI and TaqI, indicate that the technique has sufficient sensitivity to detect single-copy genes present within genomic digests. At the optimal hybridization temperature for the oncogene sequence it has found that the addition of 5 µg of restricted total human DNA did not increase the background noise present in PUCLM8 Hind III cRNA/pT24 Bam HI DNA hybridizations.

Figure 8B:
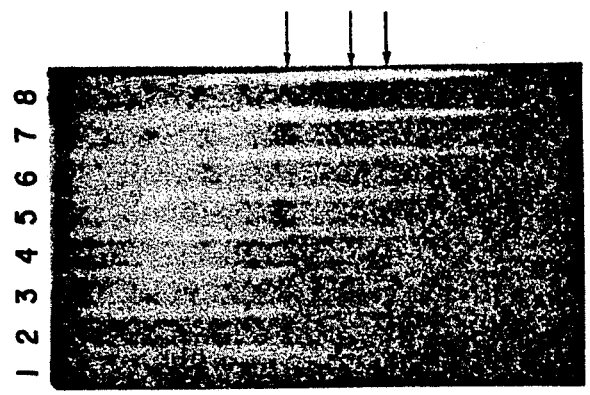
FIG. 8 is an autoradiogram demonstrating the hybridization of PUCLM8 Hind III cRNA and total human DNA digested with Bam HI and Taq I.
Figure 8A:
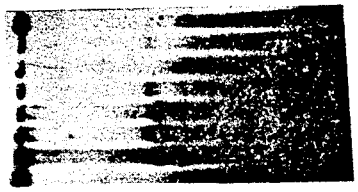

FIG. 8 illustrates the hybridization pattern obtained when PUCLM8 Hind III cRNA is hybridized to total human genomic DNA digested within Bam HI and Taq I.

The cRNA used in all hybridization reactions was synthesized from a PUCLM8 Hind III-digested DNA template, treated with DNAase I and precipitated with LiCl. $5\times10^6$ dpm of cRNA were used in all reactions. The test DNA was either Bam HI-digested pT24 or total Human DNA digested with either Bam HI or Taq I. Hybridizations were performed for 3 hours at either 56° C. or 59° C. in 10 μl of hybridization buffer prescribed in the Detailed Description of the Invention supra. Reactions were treated with 5 μg/ml RNAase A in a volume of 20 μl in the presence of 40% formamide and 0.2 m NaCl for 30 minutes at 22° C. Samples were brought to 36 μl upon addition of 10 μl TBE buffer and 6 μl 6x loading buffer. Samples were electrophoresed on a 1% agarose gel-TBE at 200 volts for 2 hours. The autoradiogram above is a 16 hour exposure. The hybridization reactions were as follows: Lane 1: cRNA without test DNA; Lane 2: cRNA vs 10 pg pT24 Bam HI-digested DNA; Lane 3: cRNA vs 10 pg pT24 Bam HI-digested DNA and 5ug total human DNA digested with Bam HI; Lane 4: cRNA vs 10 pg pT24 Bam HI-digested DNA and 5 ug total human DNA digested with Taq I; Lanes 5 and 7: cRNA vs total human DNA digested with Bam HI (5 ug), hybridized at 59° C. and 56° C., respectively; Lanes 6 and 8: cRNA vs 5 μg total human DNA digested with Taq I hybridized at 59° C. and 56°, respectively. The addition of total human DNA digested with either Bam HI or Taq I did not increase the background noise of the cRNA-pT24 Bam HI-digested DNA hybridization reaction (Lane 3 and 4 vs Lane 2). Both Taq I and Bam HI-digested total human DNA contain specific restriction fragments to which the cRNA probe hybridizes.

What is claimed is:

1. In a method for the detection of nucleic acids by hybridization the improvement comprising:
   providing a discrete RNA probe;
   contacting said discrete RNA probe with the nucleic acid to be detected in solution under hybridizing conditions; forming a hybrid; and detecting the hybrid after electrophoresis.

2. The method according to claim 1 wherein said electrophoresis is performed at or near a temperature which promotes the formation of said hybrids thereby maintaining the integrity of the hybrids during said electrophoresis.

3. The method according to claim 1 further comprising sizing the DNA in the hybrid wherein after eletrophoresis the rate of migration of said hybrid is compared with hybrids consisting of said cRNA probe and DNAs of predetermined size.

4. The method according to claim 1 wherein the nucleic acid to be detected is DNA and said hybridization conditions promote the formation of RNA-DNA hybrids.

5. The method according to claim 4 wherein said hybridization conditions comprise:
   incubating a cRNA probe of discrete size with a sample of DNA to be detected which contains a nucleotide base sequence complementary to that sequence present in said probe, in a buffer comprising salts and formamide under conditions of time and temperature which result in the denaturation of the DNA;
   shifting the temperature for a sufficient time to permit the formation of DNA/RNA hybrids, said temperature being above the temperature necessary for DNA-DNA strand separation and terminating the hybridization conditions.

6. The method according to claim 5 including the further step of treating said DNA/RNA hybrids with ribonuclease.

7. The method according to claim 5 wherein said formamide is present in a concentration of about 80% and said DNA/RNA hybrid formation temperature is between about 52° C. and about 60° C.

8. The method according to claim 4 wherein said probe is provided by:
   inserting a segment of the DNA to be detected into a vector;
   molecularly cloning the inserted segment;
   transcribing the inserted DNA under transcription conditions to provide a discrete cRNA probe; and
   recovering the cRNA probe so produced.

9. The method according to claim 8 wherein said transcription conditions comprise:
   (a) providing a transcription template by endonuclease digestion of a vector containing the DNA segment to be transcribed;
   (b) incubating said template in a reaction mixture comprising RNA polymerase, four types of nucleotide triphosphates at least one of which is detectably labelled, and a buffer for a sufficient period of time and at sufficient temperature to provide for the synthesis of full-length transcripts,
   (c) terminating the reaction and recovering the transcripts so produced.

10. The method according to claim 9 which includes the further step of purifying said cRNA transcripts comprising:
    (a) treating the terminated reaction mixture with deoxyribonuclease;
    (b) extracting the cRNA;
    (c) precipitating the extracted cRNA by reaction with LiCl, and recovering the purified cRNA.

11. The method according to claim 8 wherein said cRNA probe is labelled with an analytically detectable reagent.

12. The method according to claim 11 wherein the cRNA probe is labelled by the introduction of said analytically detectable reagent into the cRNA during said cRNA's formation.

13. The method according to claim 11 wherein the cRNA probe is labelled with said analytically detectable reagent after said cRNA probe has been formed.

14. The method according to claim 11 wherein said cRNA is labelled with a radioactive label.

15. The method according to claim 11 wherein said label is $^{32}P$.

* * * * *